United States Patent [19]
Wochnowski

[11] 3,950,698
[45] Apr. 13, 1976

[54] ARRANGEMENT FOR DETERMINING THE MOISTURE CONTENT OF TOBACCO AND THE LIKE

[75] Inventor: Waldemar Wochnowski, Hamburg, Germany

[73] Assignee: Hauni-Werke Korber & Co. KG, Hamburg, Germany

[22] Filed: Mar. 22, 1974

[21] Appl. No.: 454,239

[30] Foreign Application Priority Data
Mar. 27, 1973  Germany............................ 2315155

[52] U.S. Cl.................. 324/61 R; 177/50; 317/246
[51] Int. Cl.². ......................................... G01R 27/26
[58] Field of Search ......... 324/61 R, 61 P; 317/246; 131/22 R, 135; 198/39; 214/2; 177/50

[56] References Cited
UNITED STATES PATENTS

| | | | |
|---|---|---|---|
| 2,219,497 | 10/1940 | Stevens et al. | 324/61 P |
| 2,653,298 | 9/1953 | McKinley | 324/61 P |
| 3,246,216 | 4/1966 | Mead et al. | 317/246 |
| 3,320,528 | 5/1967 | Esenwein | 324/61 R |
| 3,376,503 | 4/1968 | Lundstrom | 324/61 R |
| 3,482,162 | 12/1969 | Wochnowski | 324/61 R |
| 3,522,854 | 8/1970 | Liedtke | 131/22 R |

*Primary Examiner*—Stanley T. Krawczewicz
*Attorney, Agent, or Firm*—Kane, Dalsimer, Kane, Sullivan and Kurucz

[57] ABSTRACT

The arrangement determines the moisture content of tobacco, in either leaf- or comminuted form, tobacco substitutes, other smokers' products, filter materials, cigarette and cigar papers and wrappings, related and analogous fibrous and other materials, and the like. The material in question is supported by a supporting arrangement. First and second electrodes are connected to an A.C. voltage source to form a capacitor. The electrodes are so disposed that the electric field joining the electrodes travels through the material being supported. The moisture of the material is determined by determining the effect upon the capacitor of the moisture in the material being supported and penetrated by the electric field. An arrangement is provided for compressing the material in question while the material is actually being supported and penetrated by the electric field.

14 Claims, 5 Drawing Figures

ARRANGEMENT FOR DETERMINING THE MOISTURE CONTENT OF TOBACCO AND THE LIKE

BACKGROUND OF THE INVENTION

My issued U.S. Pat. No. 3,777,258 discloses an arrangement for determining the amount of moisture in tobacco or other smoking goods, making use of a support for the tobacco and associated first and second electrodes which together with the tobacco itself form a capacitor of an electrical resonant circuit, and also making use of a measuring instrument for measuring at resonance an electrical signal of the resonant circuit which is indicative of the amount of moisture in the tobacco. In such an arrangement, the two electrodes of the measuring capacitor are associated with a bounding surface of the body or stream of tobacco, whereas means for pressing the tobacco cooperates with the tobacco support.

The entire disclosure of my above-identified United States patent is incorporated herein by reference.

SUMMARY OF THE INVENTION

An object of the present invention is to provide an arrangement of the type disclosed in my above-identified U.S. patent, but of more reliable operation, and in particular adapted for the measurement of the quantity of moisture present in very moist tobacco, and the like.

This object can be met, according to one advantageous concept of the invention, by providing, as the means for pressing the tobacco, a rotating hollow body, in the interior of which are provided the two electrodes of the measuring capacitor, the two electrodes being arranged facing towards the tobacco.

It is desired according to the invention that the electric field lines passing through the hollow rotating body be weakened as little as possible in consequence of such passage. To this end, it is contemplated, as one possiblity, to configurate the hollow rotating body in the form of a drum whose circumferential wall is comprised of a material having a dielectric characteristic at least approximately equal to that of air. This condition can be met, as one possibility, by a drum whose circumferential wall is comprised of polypropylene.

A certain averaging out of the measured value, in order to avoid the inaccurate measurements which might otherwise result when dealing with tobacco comprised of adjoining zones of markedly different moisture content, can be achieved according to a further concept of the invention by dividing the first of the two electrodes into a plurality of electrically interconnected part electrodes, these part electrodes together with the second electrode being arranged along a curved surface corresponding to the curve of the drum wall. The resulting advantageous effect can be further increased by likewise dividing the second electrode into a plurality of electrically interconnected second part electrodes arranged pairwise with the first part electrodes in the aforementioned surface.

In modern tobacco-processing installations, the processing of the tobacco is performed, to the extent possible, while the tobacco is being uninterruptedly conveyed. It is a particular object of the invention to measure the moisture content of the tobacco, as the tobacco is being conveyed, with the least possible disturbance in the conveyance of the tobacco. To this end, it is of advantage that the support for the tobacco be a tobacco conveyor, preferably an endless tobacco conveyor. In order to adjust the arrangement for varying amounts of conveyed tobacco, it is contemplated to mount the rotating drum, with its two interior electrodes, for movement in direction towards and away from the tobacoo conveyor.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
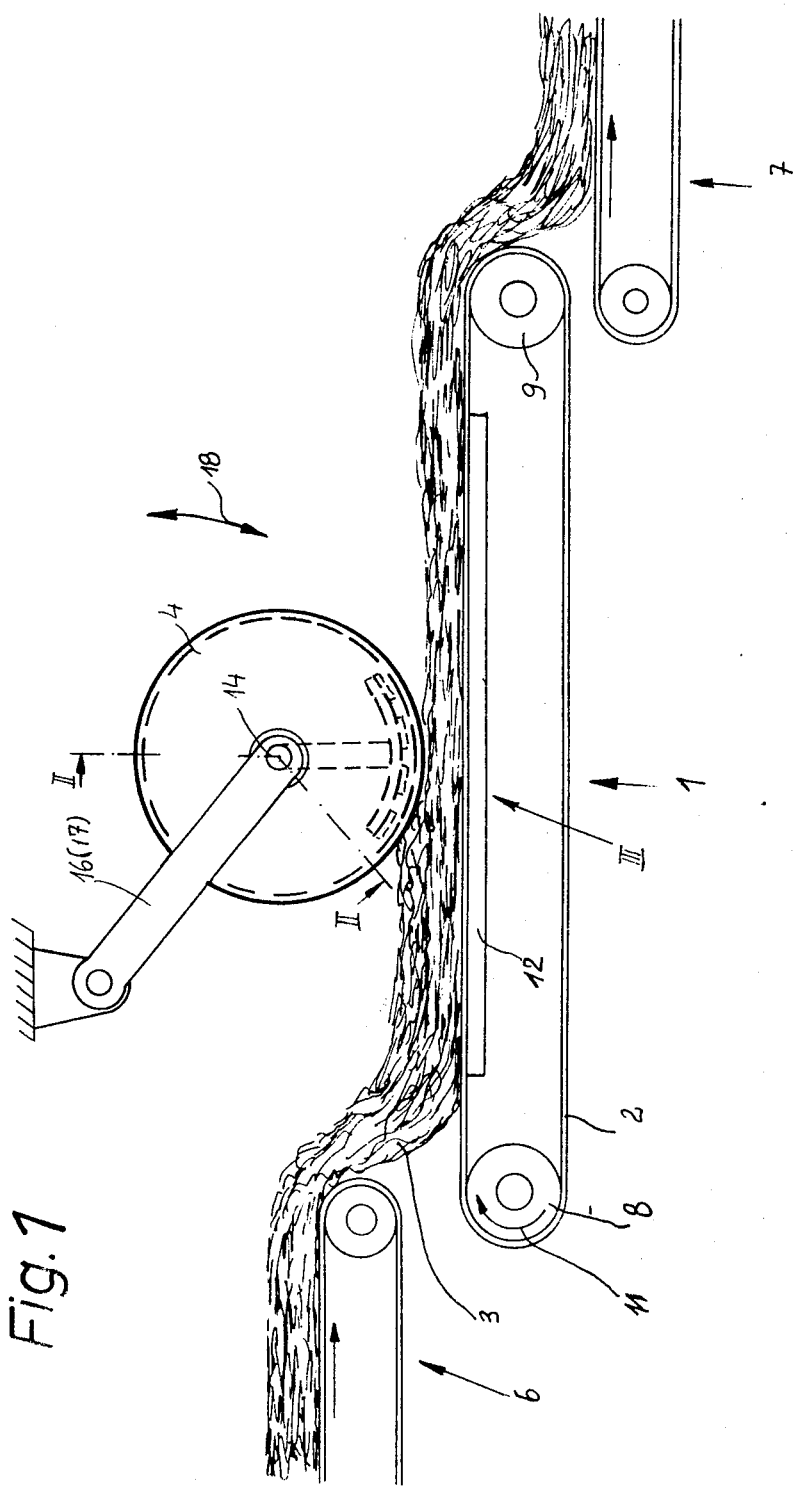
FIG. 1 depicts a first embodiment of the invention.

The arrangement depicted in FIG. 1 is comprised of a tobacco support 1 in the form of a conveyor belt 2 of an endless conveyor arrangement for tobacco 3. Means is provided for pressing the tobacco 3 against the tobacco support 1, this pressing means having the form of a rotating hollow body 4, here in the form of a drum. The arrangement further includes a conveyor arrangement 6 for transporting tobacco to the measuring station, and a further conveyor arrangement 7 for transporting tobacco away from the measuring station. The conveyor belt 2 is guided by guide rollers 8 and 9, of which the roller 8 is a drive roller which is driven in the direction of arrow 11. The upper run of the conveyor belt 2 is guided over a support slab 12 which is provided to resist the pressing force with which the drum 4 presses down upon the tobacco 3.

Figure 2:
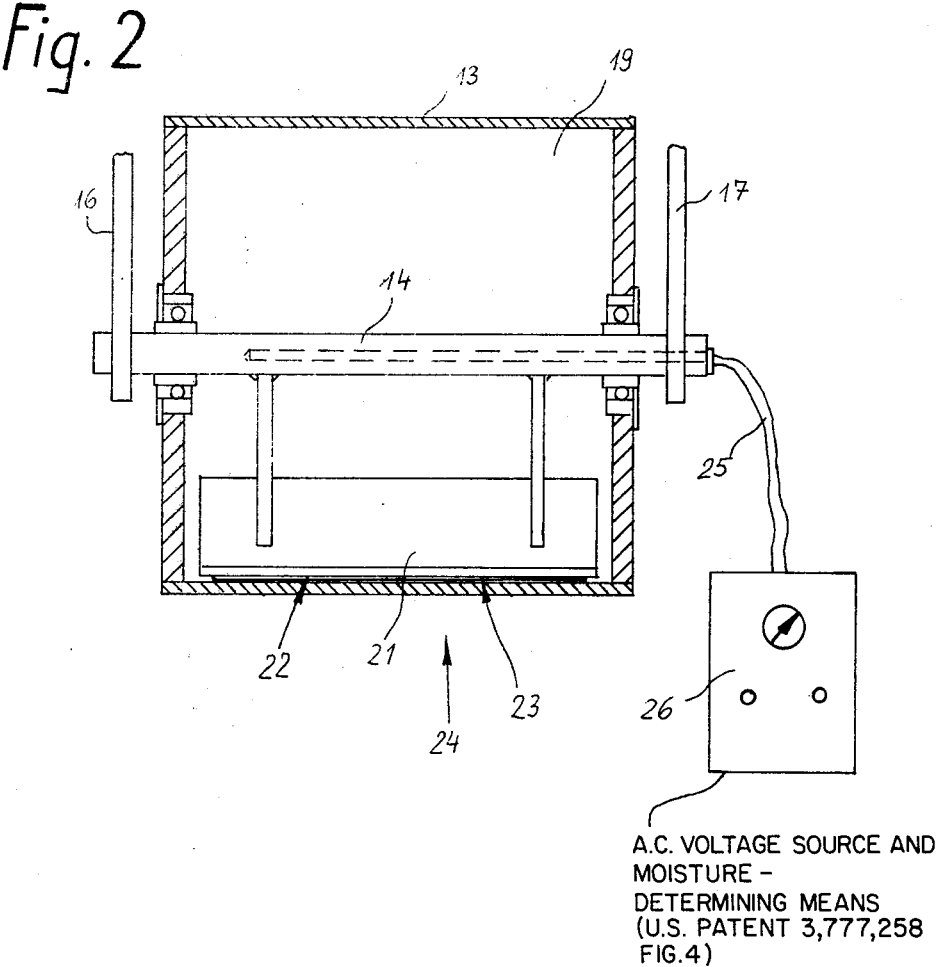
FIG. 2 is a section taken through the pressing means of FIG. 1, the section being taken along line II—II of FIG. 1.
Figure 3:
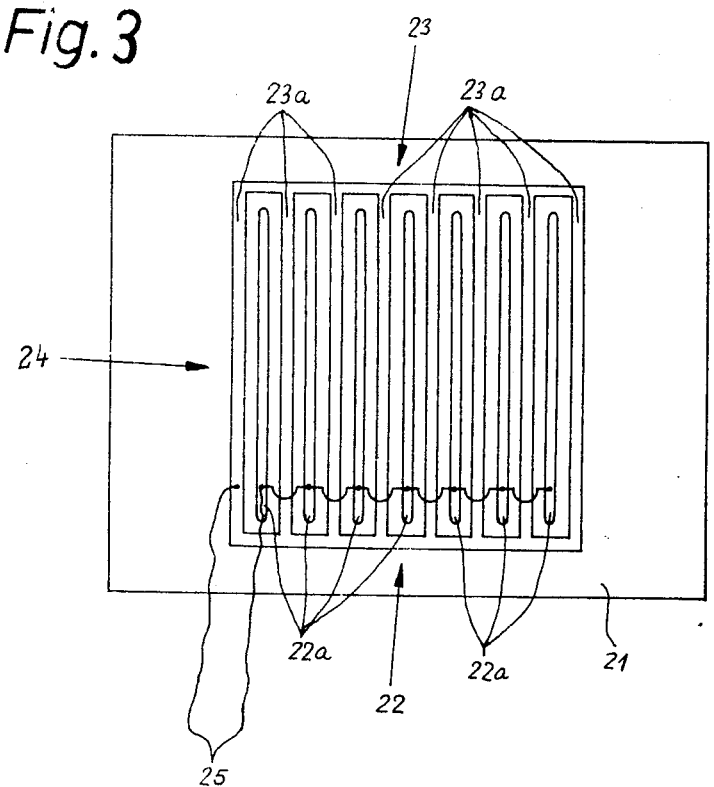
FIG. 3 is a view from above of the electrode arrangement employed in FIGS. 1 and 2.

The construction of the drum 4 is best seen in the sectional view of FIG. 2. The drum 4 has a circumferential wall 13 comprised of polypropylene, a material having substantially the same dielectric characteristics as air. The drum 4 is rotatably mounted upon a shaft 14, which in turn is mounted for swinging movement in the direction of double-headed arrow 18 (FIG. 1) by means of lever arms 16, 17. Ordinarily, the weight of the drum 4 itself will be sufficient to cause the drum to press down upon and compress the tobacco 3 on the upper run of the conveyor belt 2. Accordingly, the circumferential wall 13 of the drum 4 constitutes a boundary surface for the tobacco. Stationarily supported on the shaft 14, in the interior 19 of the drum 4, is an insulating plate 21 having good high-frequency characteristics. The insulating plate 21 is curved in conformity to the curve of the circumferential wall 13 of the drum 4. Mounted on the underside (as seen in the drawings) of the insulating plate 21 are the first and second electrodes 22, 23 (details of which are shown in FIG. 3). The electrodes 22, 23 form a measuring capacitor or condenser 24 and are connected by means of an electrical conductor 25 with a measuring arrangement 26 of per se known type, for example comprised of a high-frequency generator, a measuring resonant circuit and a tube voltmeter. A suitable measuring arrangement is disclosed in my above-identified U.S. patent. The capacitor structure 24 herein corresponds to the capacitor structure 27 of my U.S. Pat. No. 3,777,258, and can be connected without modification in place of capacitor 27 in the A.C. source and measuring means shown in the circuit diagram of FIG. 4 of that patent.

FIG. 3 depicts the insulating plate 21 with the electrodes 22, 23 mounted thereon, as it would be viewed from below, i.e., in the direction of arrow III in FIG. 1. The electrodes 22, 23, which form the measuring capacitor 24, are each comprised of a plurality of electrically interconnected part electrodes 22a, 23a, respectively, with each such part electrode 22a being arranged between two part electrodes 23a.

Figure 4:
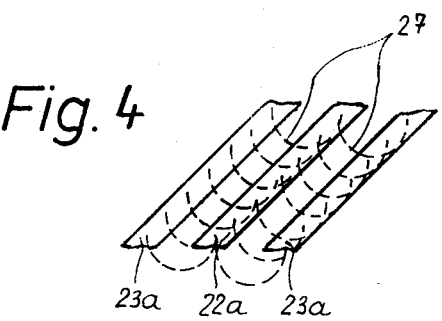
FIG. 4 is a perspective view of the electrodes of FIG. 3, with the field lines of an A.C. electrical field indicated.

FIG. 4 depicts the direction of the field lines 27 of an A.C. electric field established between adjoining part electrodes 22a, 23a.

The arrangement depicted in FIGS. 1-4 performs in the following manner:

The conveyor arrangement 6 conveys tobacco 3 in an uninterrupted stream onto the conveyor belt 2. Depending upon the thickness of the layer of tobacco 3, the drum 4 will rise to a greater or lesser extent, but on account of the weight of the drum 4 itself, the drum will exert a substantially constant downwards pressure upon the tobacco stream. The drum 4 is caused to rotate by virtue of its contact with the moving stream of tobacco 3; as an alternative possibility, however the drum 4 could be rotated by drive means, in synchronism with the travel of the conveyor belt 2.

A high-frequency voltage is applied across the capacitor electrodes 22, 23, thereby establishing between adjoining part electrodes 22a, 23a a high-frequency electric field (see FIG. 4). The field lines 27 of the A.C. electric field pass through the circumferential wall 13 of the drum 4, enter into the tobacco 3, and pass through the tobacco 3 and then out of the same, and then back through the wall 13 of drum 4. The resulting signal derived from the measuring instrument 26 can then be employed to control various tobacco-processing operations, such as for example moisturizing, drying, casing or flavoring of the tobacco.

A particular advantage of the invention lies in the arrangement of the electrodes of the measuring capacitor in the interior of a rotating body serving to compress the tobacco, here a rotating drum, since such drum can be made of a material having substantially the same dielectric characteristics as air, thereby avoiding a weakening of the electric field strength of the measuring capacitor. Furthermore, the type of compressing means contemplated by the invention has the additional advantage that the pressing operation does not interfere with the conveyance of the stream of tobacco 3 past the measuring capacitor, especially in the case of very moist tobacco which, if it were to be slid along stationary surfaces, would tend to adhere to such surfaces and become curled.

Figure 5:
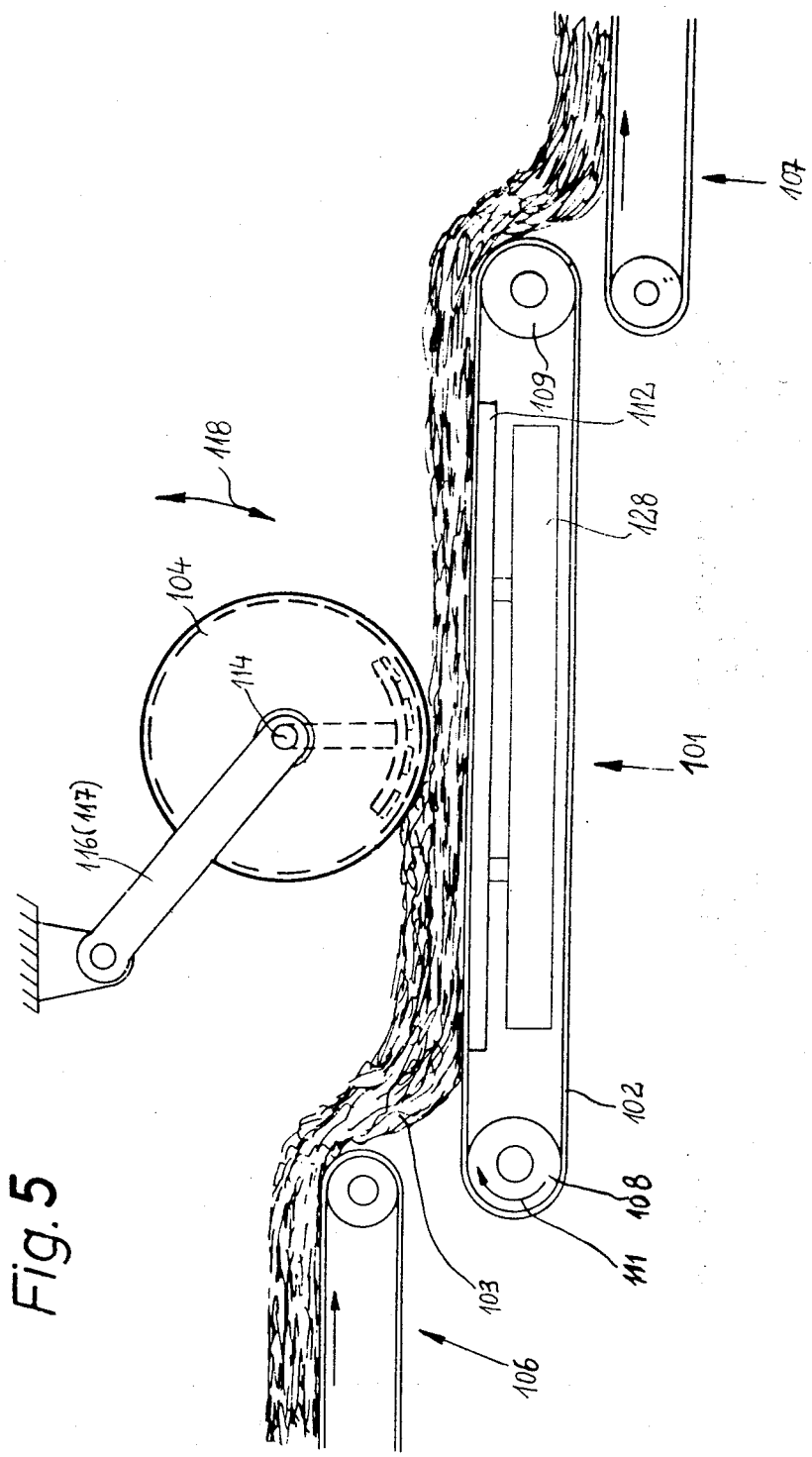
FIG. 5 shows an arrangement like that of FIG. 1 in combination with a weighing arrangement.

FIG. 5 depicts a modification of the arrangement shown in FIG. 1, corresponding parts being identified with the same reference numeral, but increased by 100.

In FIG. 5 the drum 104 advantageously cooperates with a conveyor-type weighing arrangement 128 in such a manner that the slab 112 which serves to counter the drum 104 also serves as a part of the weighing arrangement. In this way it is possible to continuously measure both the weight and the moisture content of a stream of tobacco 103 at a single measuring station as it is carried on the conveyor belt 102. The results of such measurements may then be employed for quality control purposes, or to regulate other tobacco-processing operations.

It will be understood that each of the elements described above, or two or more together, may also find a useful application in other types of constructions differing from the types described above.

While the invention has been illustrated and described as embodied in an arrangement for measuring the moisture content of tobacco, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of the invention and, therefore such adaptations should and are intended to be comprehended within the meaning and range of equivalence of the following claims.

What is claimed as new and desired to be protected by Letters Patent is set forth in the appended claims:

1. An arrangement for determining the moisture content of fibrous material and the like, particularly tobacco, other smokers' products and the like, comprising in combination, supporting means for supporting such material; and A.C. voltage source; first and second electrodes connected to said voltage source to form a capacitor, said electrodes being so disposed that the electric field joining said electrodes travels through material being supported by said supporting means; means for determining the moisture of such material by determining the effect upon said capacitor of moisture in material supported by said supporting means and penetrated by said field; and compressing means located and arranged for compressing such material while the material is being supported by said supporting means and penetrated by said field, wherein said compressing means comprises a rotating hollow body mounted to bear towards said supporting means at the location where said field penetrates material being supported by said supporting means, and wherein said first and second electrodes are stationarily mounted inside said rotating hollow body.

2. An arrangement as defined in claim 1, wherein said hollow body is mounted to bear downwards under its own weight towards said supporting means at the location where said field penetrates material being supported by said supporting means.

3. An arrangement as defined in claim 1, wherein said rotating hollow body is a rotating hollow drum.

4. An arrangement as defined in claim 1, wherein said rotating hollow body is comprised of a material having dielectric characteristics substantially the same as those of air.

5. An arrangement as defined in claim 4, wherein said material is polypropylene.

6. An arrangement as defined in claim 1, wherein said first electrode is comprised of a plurality of electrically interconnected part electrodes stationarily mounted in the interior of said hollow rotating body and positioned along a curved surface corresponding to the curved periphery of said body and spaced from said second electrode.

7. An arrangement as defined in claim 6, wherein said second electrode is comprised of a plurality of electrically interconnected part electrodes stationarily mounted in the interior of said hollow rotating body and positioned along said curved surface and arranged in pairs with respective ones of the part electrodes of said first electrode.

8. An arrangement as defined in claim 1, wherein said supporting means comprises conveying means for conveying material along a predetermined path.

9. An arrangement as defined in claim 1, wherein said supporting means comprises endless conveyor means for conveying material along a predetermined path.

10. An arrangement as defined in claim 9, wherein said rotating hollow body together with said electrodes are mounted for joint movement towards and away from said endless conveyor means.

11. An arrangement as defined in claim 1, and further including means for weighing such material while it is supported by said supporting means and penetrated by said field.

12. An arrangement as defined in claim 11, wherein said supporting means comprises endless conveyor means for conveying material along a predetermined path, said endless conveyor means being comprised of an elongated conveyor member having one side facing said hollow rotating body and an opposite side, and wherein said weighing means comprises a weighing arrangement located adjacent said opposite side and operative for weighing material as such material is being supported by said conveyor member.

13. An arrangement as defined in claim 12, wherein said weighing arrangement comprises a plate-shaped member contacting said opposite side of said conveyor member and serving to support material being conveyed on said conveyor member.

14. An arrangement as defined in claim 1, wherein said A.C. voltage source and said means for determining together comprise high-frequency oscillator means for creating a high-frequency electrical signal, circuit means connected to said capacitor to form with the latter a tuned circuit connected to said high-frequency oscillator means, frequency control means connected to said tuned circuit for controlling the resonant frequency of said tuned circuit in such a manner that said tuned circuit is in resonance with said high-frequency electrical signal, and measuring circuit means connected to said tuned circuit for furnishing an electrical signal during said resonance, said electrical signal having a characteristic varying as a function of the moisture content of material supported by said supporting means.

* * * * *